United States Patent [19]
Trautman

[11] Patent Number: 5,121,470
[45] Date of Patent: Jun. 9, 1992

[54] AUTOMATED INTERACTIVE RECORD SYSTEM

[75] Inventor: Edwin D. Trautman, Lexington, Mass.

[73] Assignee: Intellimetrics Instrument Corporation, Billerica, Mass.

[21] Appl. No.: 473,651

[22] Filed: Feb. 1, 1990

[51] Int. Cl.⁵ ............................................. G06F 15/20
[52] U.S. Cl. ..................................... 395/140; 395/155
[58] Field of Search ................... 364/518, 521, 413.01, 364/413.02, 413.06; 395/140, 155, 156, 160, 161

[56] References Cited

U.S. PATENT DOCUMENTS

| | | |
|---|---|---|
| 4,347,568 | 8/1982 | Giguere et al. ................... 364/900 |
| 4,835,683 | 5/1989 | Phillips et al. ................... 364/200 |
| 4,858,121 | 8/1989 | Barber et al. ................... 364/413.01 X |
| 4,878,175 | 10/1989 | Norden-Paul et al. ........ 364/413.01 X |

*Primary Examiner*—Heather R. Herndon
*Attorney, Agent, or Firm*—Iandiorio & Dingman

[57] ABSTRACT

An automated interactive record system for automatically indexing a set of data obtained from a number of internal and external input sources. A set of data is organized along at least one indexing dimension. Specific data events are identified from the set of data according to predetermined methods. An index of data objects associated with the specific data events is then established. The index of data objects is then displayed along the indexing dimension and actuators are defined for manipulating the data objects that are associated with specific data events.

34 Claims, 10 Drawing Sheets

AUTOMATED INTERACTIVE RECORD SYSTEM

FIELD OF INVENTION

This invention relates to an automated interactive recover system, and more particularly to a system that displays data along at least one indexing dimension and allows ready access to associated data relative to some point or set of points along the dimension and the input of data to be displayed at given locations upon the dimension.

BACKGROUND OF INVENTION

In the medical care field, data on a patient's recovery or condition is often entered by hand after performing a therapeutic function or observing various monitors and measuring devices. This data is combined into a series of data collections often without easy access to any single piece of data or a method of correlating data from different places within the collection as a whole. This lack of organization and easy access makes it difficult for health care personnel to quickly identify trends and key events in the patient's condition. Further, the prospective administration of procedures, medication or tests may also prove troublesome since this type data is not generally combined or correlated with already existing monitor data that is gathered on the patient. This monitor data, however, could in fact be a necessary precondition to performing this prospective administration of care.

Even when health care personnel store patient data on a computer, it is not adequately organized and presented with respect to the overall process of monitoring condition or recovery, which is often represented by a strip chart recording of a certain vital sign. Hence, correlating other data with a given time period on the strip chart recording often proves difficult and comparing this set of data in order to reach general conclusions, once it is correlated with similar data taken at earlier intervals, proves even more troubling. In specific areas of medical care, technology is now available to monitor several parameters of the subject's condition through a computer. However, the problem with many computer monitoring systems is the continuing inability of the user to correlate the many layers of interconnected data in a manner in which the initial broad perspective of the data is not lost. This is the problem encountered with hypermedia in which, as progressively smaller concentrations of data are viewed, the large picture becomes lost, thus leading to viewer disorientation and confusion. A system is required to retain perspective with the larger view of data while concurrently allowing the viewer to delve into the layers of hypermedia. A need thus arises in medicine as well as in many other areas of process control and monitoring of nonmedical systems, to devise a method to track and correlate various data from a variety of sources, including the computer's own internal calculations with reference to a time line or similar dimension that retains a larger and lasting perspective.

SUMMARY OF INVENTION

It is therefore an object of this invention to provide a system for the automatic collection, organizing and indexing of a set of acquired signal data, or other previously stored data, and display of this index data graphically on one or more axes where the viewer maintains the ability to access or input specific data objects, relative to a point or group of points, that constitute a specific event as predefined by the system.

It is a further object of this invention to provide a system which reduces viewer confusion and disorientation by maintaining a continual display of the data shown on the axis while input or accessed data objects may be viewed independently with reference to the axis.

It is a further object of this invention to provide a system which indexes data from preexisting data bases and otherwise input data.

It is a further object of this invention to provide a system which allows the input of data from a variety of both manually, internally generated, and automatically activated sources.

It is a further object of this invention to provide a system allowing input and display of data objects in a variety of manners and representations, including textual, audio, graphical and pictorial.

It is a further object of this invention to provide a system allowing the user direct screen interaction to manipulate data.

It is a further object of this invention to provide a system which provides access to and input of data in a manner highly effective in the fields of process control, medical care and other areas requiring organization of various forms of data over a dimension.

This invention results from the realization that a truly effective data management and control system may be achieved through the combination of the two powerful independent concepts of hypermedia and indexing of data along one or more dimensions, and through a system that provides for the input of data from a variety of sources and that identifies and associates these data inputs with specific points of significance along the indexing dimension to give the viewer a clear, unconfusing, display with easy access to, and control of, data.

This invention features an automated interactive record system. This system includes means for organizing a set of data along at least one indexing dimension. There are means provided for identifying specific data events from the set of data according to predetermined methods. There are means for establishing an index of data objects associated with the specific data events. There are further means for displaying this index of data objects along the indexing dimension and means for defining actuators for manipulating the data objects indexed with specific data events.

In a preferred embodiment, the means for establishing an index of data objects may further include marker means for individually marking data events. The marker means may further include means for designating the location of data associated with specific data events, means for specifying the configuration of actuators, means for determining a symbolic representation to be displayed for a given data object, and means for designating the operation to be effected for a specific data event. The means for defining actuators may further include means for bounding interactive areas on the display screen corresponding to locations along the indexing dimension, and those means for bounding may include means for operating the actuators in response to a touching of the interactive areas and in response to a contacting of the interactive areas with a cursor. The means for displaying the index of data objects and specific data events may further include means for generating descriptive pictorial icons which are symbolic representations of data objects and specific data events and which are associated with specific data events along the indexing dimension. The means for organizing a set of data may further include an indexing dimension, which is time. The means for identifying specific data events may include means for comparing the set of data to a reference and means for reviewing data objects to generate additional specific data events. The means for organizing this set of data may include means for graphically plotting the set of data on a display screen. This means for graphically plotting may further include means for graphically displaying the minimum, maximum and mean values of data over a given interval. Finally, the means for establishing an index of data objects may include a data object comprising at least one of a plurality of data fields including audio, visual, textual, numerical, algorithmic and graphical data.

DISCLOSURE OF PREFERRED EMBODIMENT

Other objects, features and advantages will occur to those skilled in the art from the following description of preferred embodiment and the accompanying drawings in which.

Figure 1:
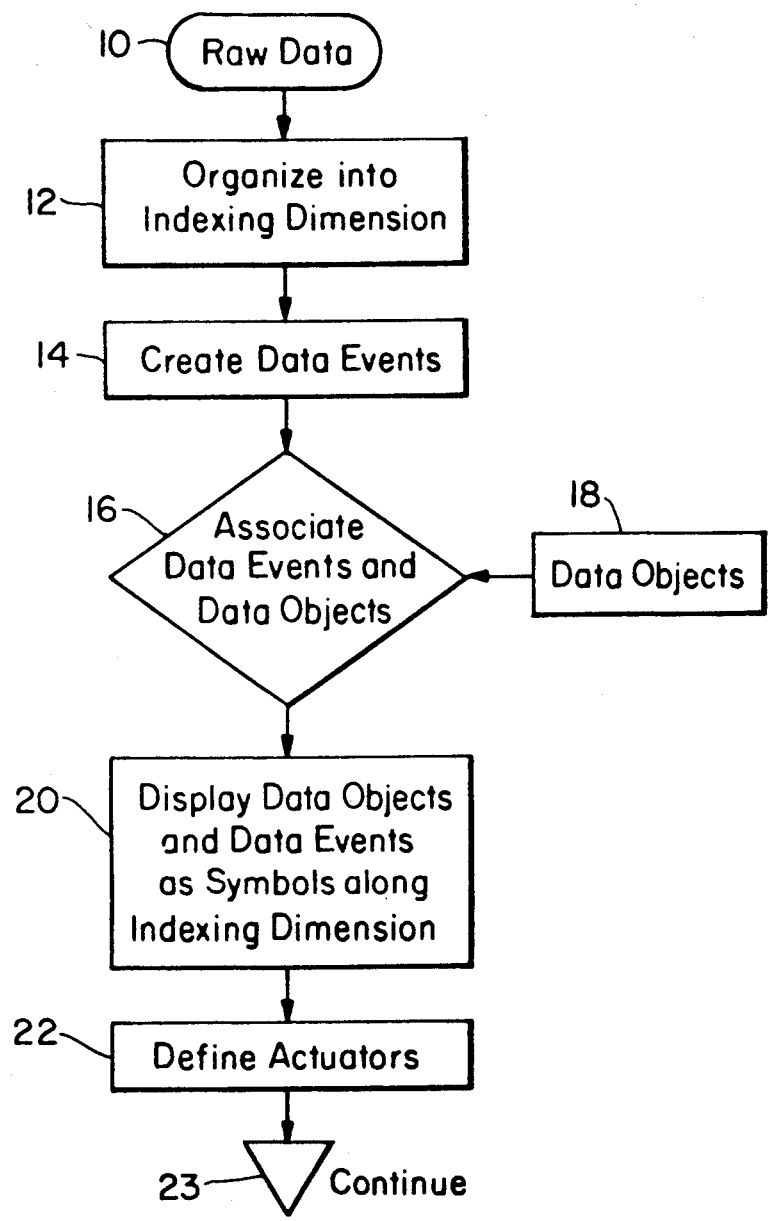
FIG. 1 is a flow chart of an interactive record system according to this invention.

In FIG. 1 there is shown a flow chart of an interactive record system according to this invention in which a set of raw data 10 is organized along an indexing dimension 12. The indexing dimension may be time or a similar dimension that may be used to organize and correlate data from a variety of sources. An indexing dimension is a variable, parameter, or characteristic intrinsic to the data which is being accumulated, that is selected because of its commonality. Other examples of such variables or parameters include sex or age of hospital patients; day or month of the year; or dimensions such as length. By means of this commonality, data from a variety of sources can be organized and correlated.

Since the interactive record system according to this invention can be used in a number of applications, an indexing dimension(s) is selected for a specific application and the system is configured to use that indexing dimension(s). In the case where time is the chosen indexing dimension, the raw data is organised and correlated in chronological fashion. From this indexing dimension, specific data events 14 are created through distinguishing sets of data into given intervals. Data objects 18 from other sources are associated 16 with specific data events according to predetermined criteria. The data objects and data events are then displayed 20 relative to the indexing dimension as symbols. These symbols are located in relation to the associated specific data events allowing the viewer to clearly see the relationship between the data objects and indexed data events. Once the data objects are displayed along the indexing dimension, actuators are created 22 to allow the data objects to be manipulated. The actuator is an interactive area, generally placed around the symbol of a data object or data event, that allows the viewer to activate the underlying data contained in the data object or referenced by the data events. The data object may be one of a variety of multimedia collections of data including pictorial, graphical, audio, textual or numerical data. The data object or data event as displayed may also prompt the viewer for further interaction and input.

Figure 2:
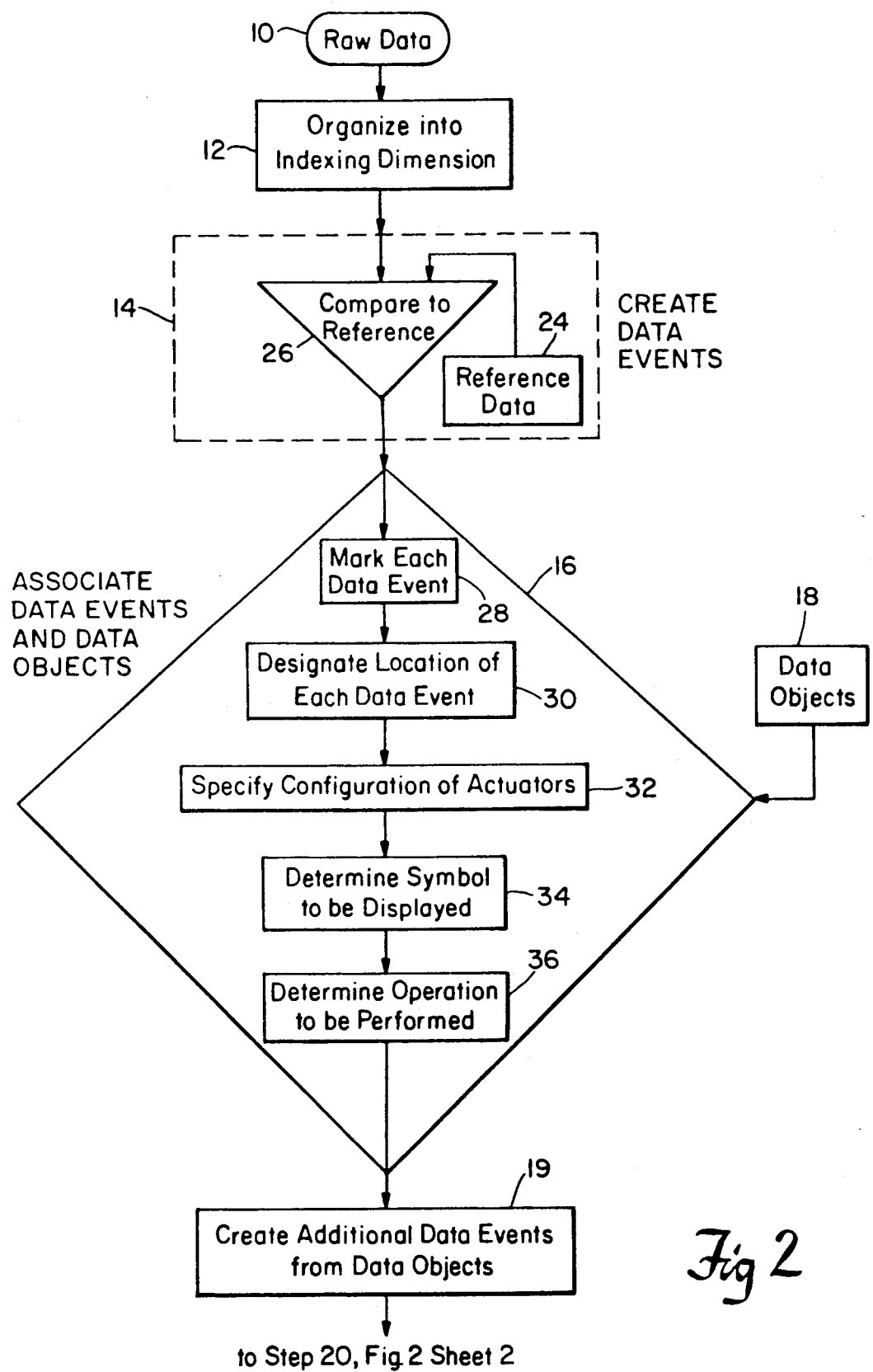
FIG. 2 is a more detailed view of the flow chart of FIG. 1.
Figure 2:
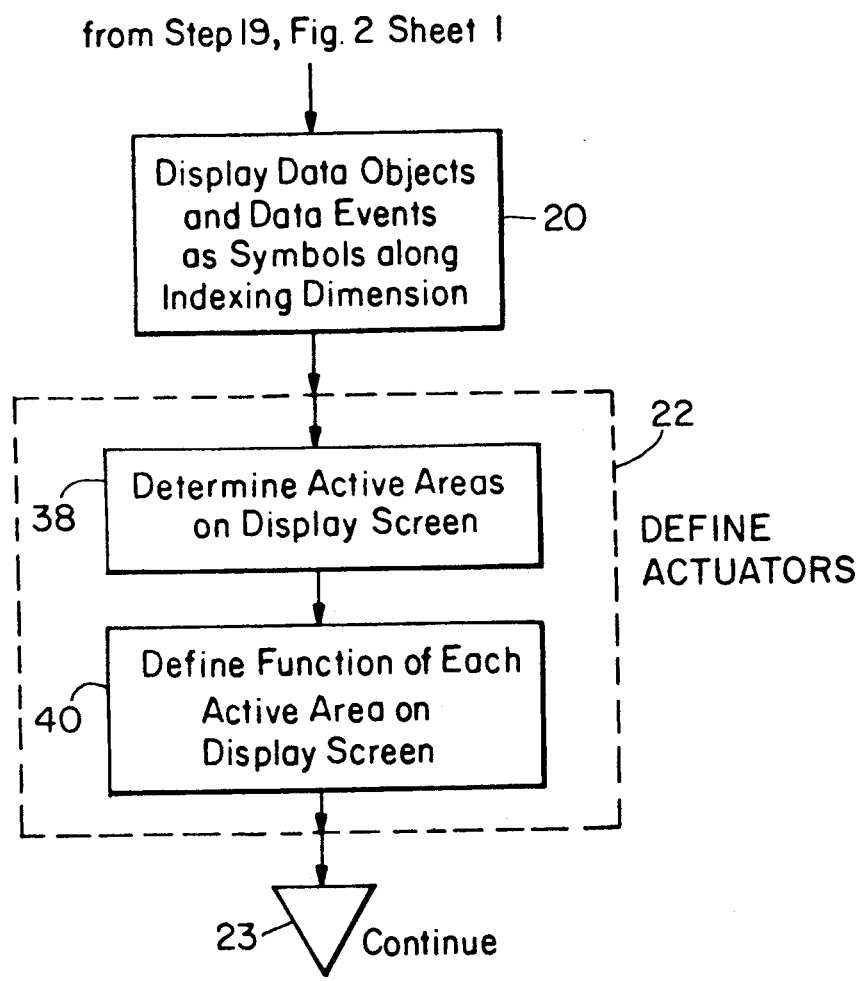

The interactive record system of FIG. 1 is shown in a more detailed flow chart in FIG. 2 in which the creation of data events 14 from an index of data along a dimension is accomplished through the comparison 26 of the indexed data with reference data 24. Data objects 18 are then associated 16 with data events. This is accomplished by marking 28 each data event to distinguish it from others and make it uniquely identifiable. Then, a location is designated 30 for each data event along the indexing dimension. The configuration of the actuators for each data event is then specified 32. The symbol to be displayed, if any, in relation to a given data event for a data object is then determined 34. Finally, the operation to be performed for each data object is determined 36. The operation performed for a data object may include the creation of additional data events 19. Data objects are reviewed and algorithmic data is retrieved and acted upon. These algorithms may specify new criteria or locations for data events which will then be noted by the system. Data objects and data events are then displayed 20 as described in FIG. 1 and actuators are defined 22. Defining of actuators is accomplished by determining the boundaries of active areas on the display screen 38 in which a given form of contact will cause an operation, and then by defining the exact function to be performed 40 for each of these active areas upon activating them.

Figure 3:
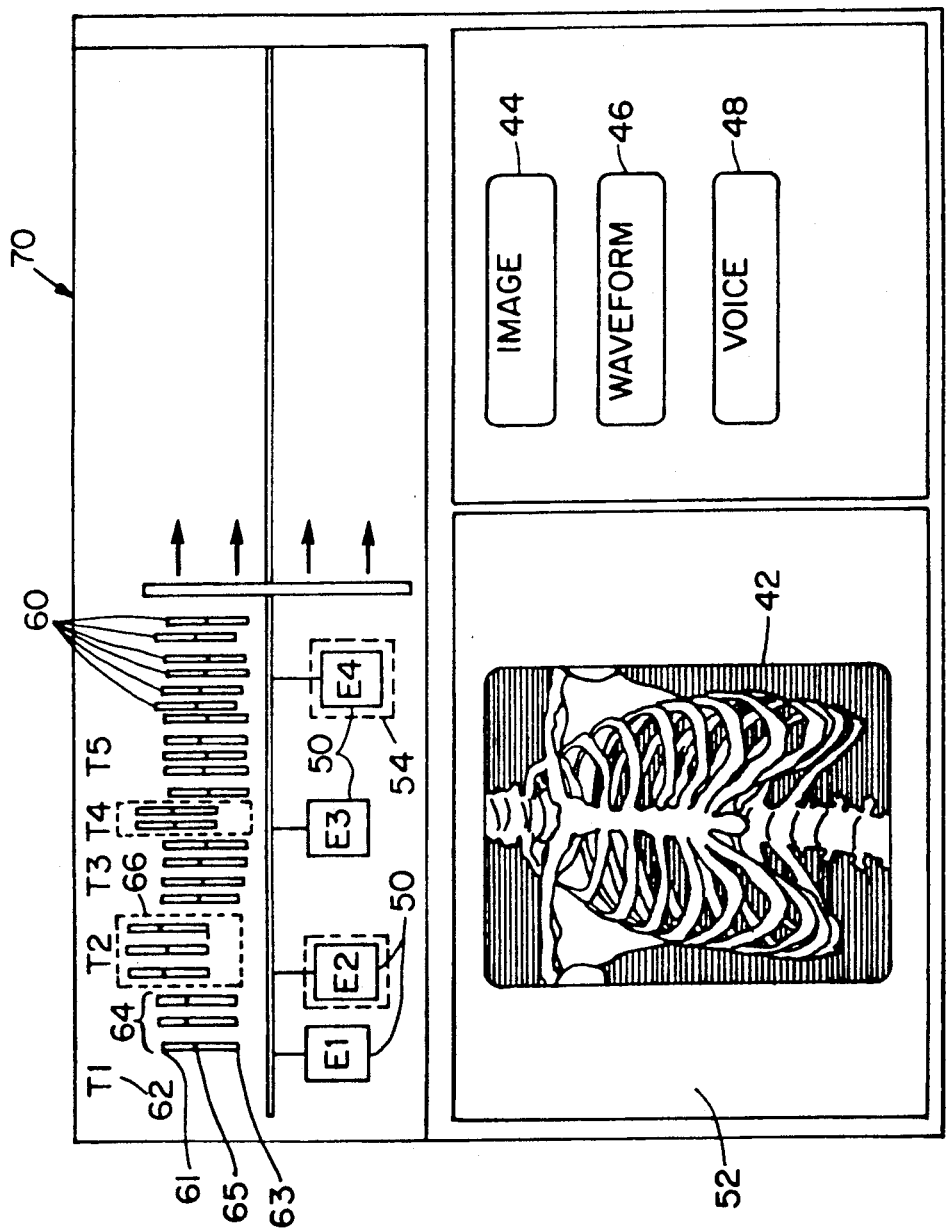
FIG. 3 is a display screen for the system generated by the system according to this invention.

FIG. 3 shows a specific example of a display screen for the system disclosed. An indexing dimension display 70 is shown along the top of the screen The upper half of this indexing dimension contains vertical line plots of data trends 60 which represent the maximum 61, minimum 63 and mean 65 values of data sampled over a given interval. This interval may represent the time of input. The dimension in this example plots continually from left to right.

The bottom half of the dimension display 70 contains pictorial icons 50 representative of data objects and data events and placed below and relative to data events with which the system has associated them. A data event in this example is represented by a grouping 64 of vertical line trends 60 that are all valued within a certain predetermined threshold level. In this example, groupings appearing beyond predetermined threshold levels form one basis for the creation of new data events.

A dotted line 66 appears around the trends comprising a data event. This dotted line is a representation of an actuator. This actuator is an unseen interactive area which, when contacted either by physical or cursor touch, will operate to display predetermined associated data objects. Similar active areas 54 exist for each of the pictorial icons 50, which, when contacted, carry out a predetermined function.

The bottom half of the display screen 52 carries a work display window, in which the contents of given data objects may be viewed or manipulated. In this particular example a pictorial data object is revealed.

The other part (right half) of bottom half of the display screen contains a series of "buttons" which in this particular example allow input of an image 44, a waveform 46 and voice 48 to form data objects. Means for other types of input may also be provided.

Figure 4:
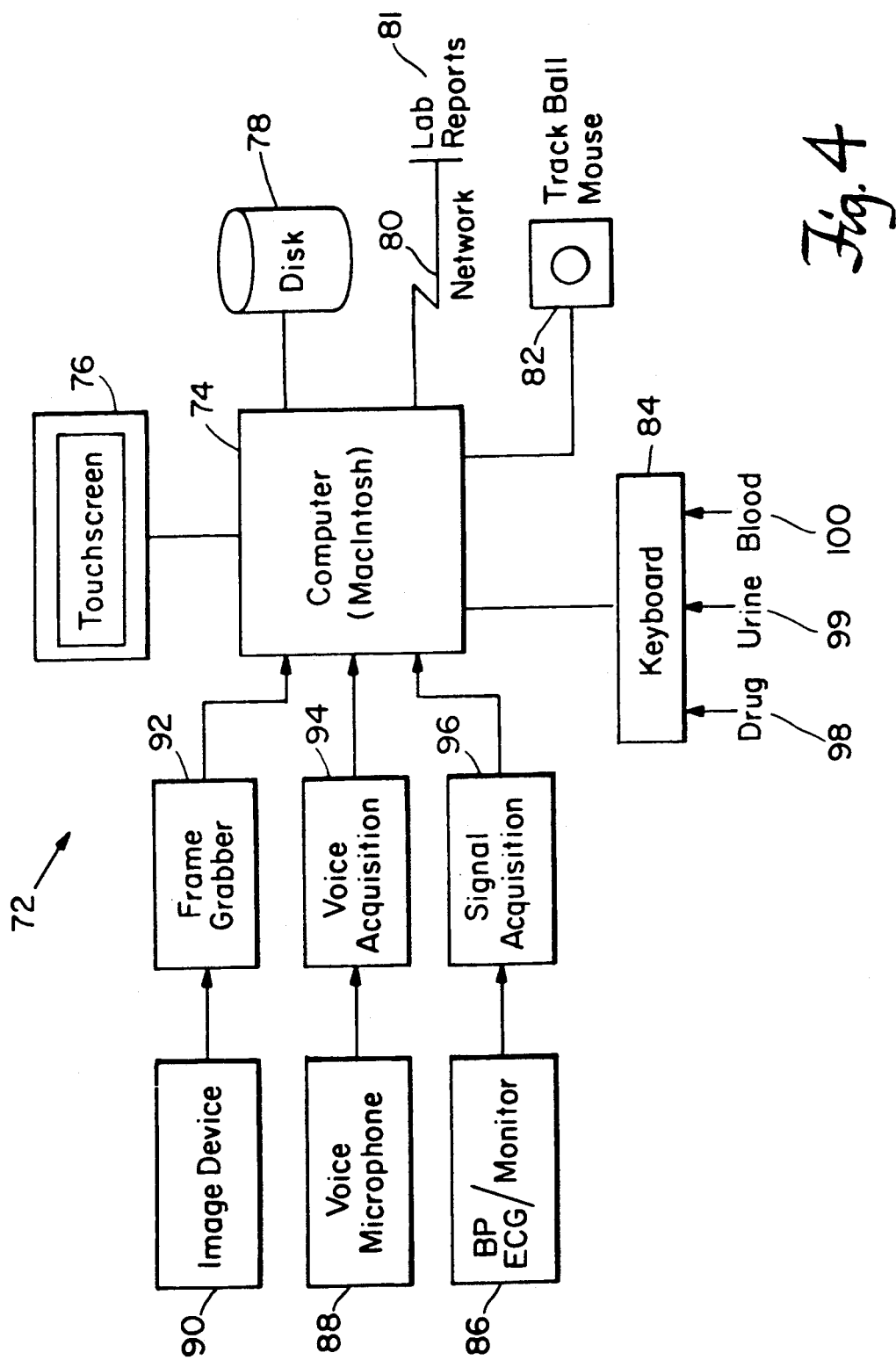
FIG. 4 is a block diagram of an interactive record system according to this invention for medical applications showing various input, output and peripheral devices.

Block diagram 72, FIG. 4, discloses a specific embodiment of the system in which a computer 74 for operating the system is provided. This computer may be an Apple Macintosh model. Data is stored on and retrieved from a disk unit 78. A touch-sensitive interactive screen 76 may be provided for direct, physical, user interaction with the data displayed. A mouse unit 82 is also provided in order to position a cursor on the interactive screen.

A keyboard 84 is provided for data entry and manipulation. In this embodiment medical information on drug 98, urine 99 and blood 100 data is input via this keyboard.

Further data, such as lab reports 81, may be accessed via a network 80 linking other data bases.

Data may also be input to the system to form data objects through a number of peripheral devices. Visual images may be input via an imaging device 90 which, through use of a frame grabber 91, creates a digitized image for storage as data in the system. Voice and similar audio inputs may be stored as data through use of a microphone 88 and voice acquisition unit 94. Various monitoring signals may also be stored by connecting the monitor 86, which in this example reads blood pressure or electrocardiogram, to a signal acquisition unit 96. Other forms of data may further be input using the proper devices and systems to create data readable by the system.

Figure 5:
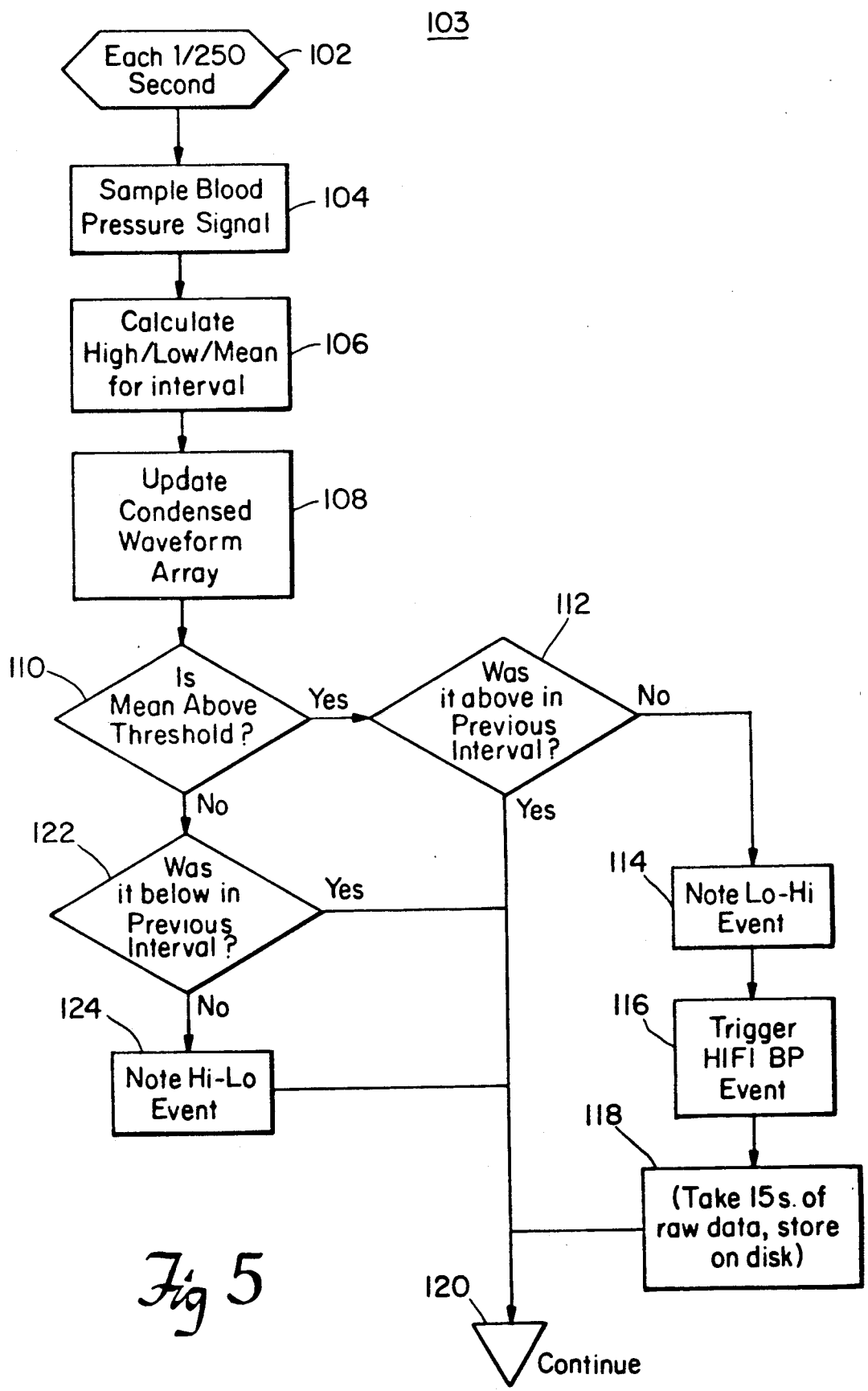
FIG. 5 is a flow chart for a specific medical application of the interactive record system according to this invention for indexing blood pressure data.

Flow chart 103, FIG. 5, constructs blood pressure trend data arrays in a specific medical example. A sample rate of one sampling each 1/250th of a second 102 is chosen in which the blood pressure signal from a monitor is read 104. The ongoing high, low and mean values for each data sampling interval (in this example, each five seconds) is calculated 106 from the signal each time a new sample is read. A condensed waveform of this signal is then updated 108 with the new piece of data. The system then determines if the latest mean value for the interval is above a predetermined threshold 110. If not, the system then determines whether the stored mean for the previous interval was below the threshold 122. If the previous interval was not below the threshold then the current interval is noted as an event from high to low 124. The system then continues by returning to the next data sample and repeating the routine 120. If the mean of the current interval is found to be above the threshold 110, then the system will determine whether it was above the threshold in the previous interval 112. If not, then the system notes an event of low to high value 114. The system then triggers a high fidelity blood pressure waveform event 116 in which fifteen seconds of raw blood pressure monitor data is taken by the system to be stored on a disk. The system then continues by returning to the next sample 120. Finally, if the system determines that the current mean is above the threshold 110 and the previous interval's mean was also above the threshold 112 then the system finds no event and simply continues 120 to the next sample.

Figure 6:
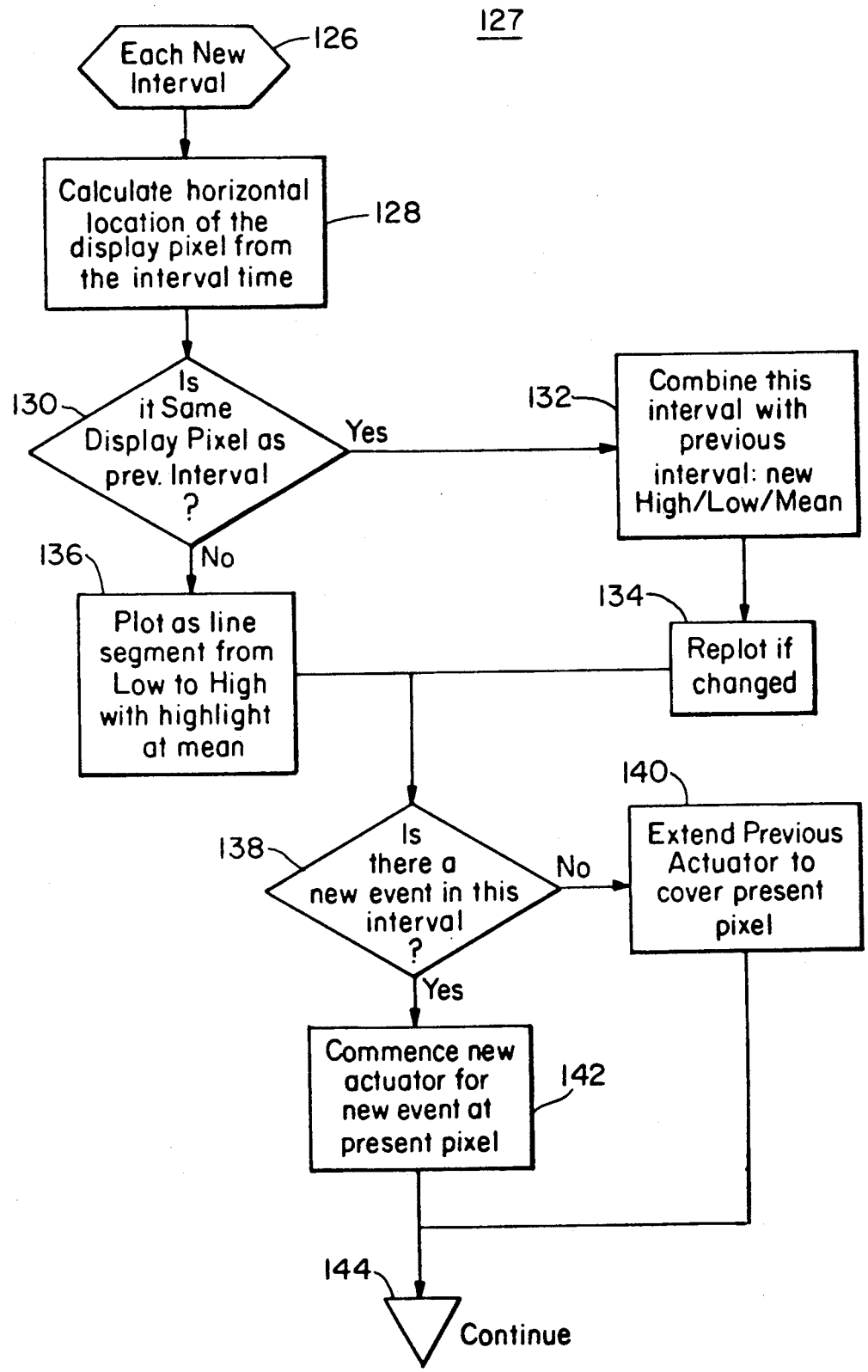
FIG. 6 is a more detailed view of the flow chart of FIG. 5 showing the formation of specific data events.

Flow chart 127, FIG. 6, updates the indexing dimension display and actuator location. When the system determines the beginning of a new data sampling interval 126 it calculates the horizontal location of the display screen interval using the interval's dimensional value, in this example its time value 128. The system then determines whether the display screen pixel is at the same location as that for the previous interval 130 since several intervals may be condensed into one pixel. If it is not the same pixel, then a new line segment from high to low with a highlighted mean value is plotted 136. If the pixel, however, is the same as that in the previous interval, then the system combines the previous and current interval and calculates a new combined high, low and mean value 132 which it replots 134 within that pixel space if necessary. Given either a new pixel or not, the system then determines whether there is a new event 138 within the interval from the notation of events as described in FIG. 5. If no new event has occurred, the actuator surrounding the plotted trends is continued to include the current pixel 140. The system then continues 144 through the routine again upon a new interval. If, however, the system determines that a new event has been noted in this interval it begins a new actuator with the present pixel 142. This new actuator activates any data objects associated with the new event. At this point the system continues 144 to the next interval.

Figure 7:
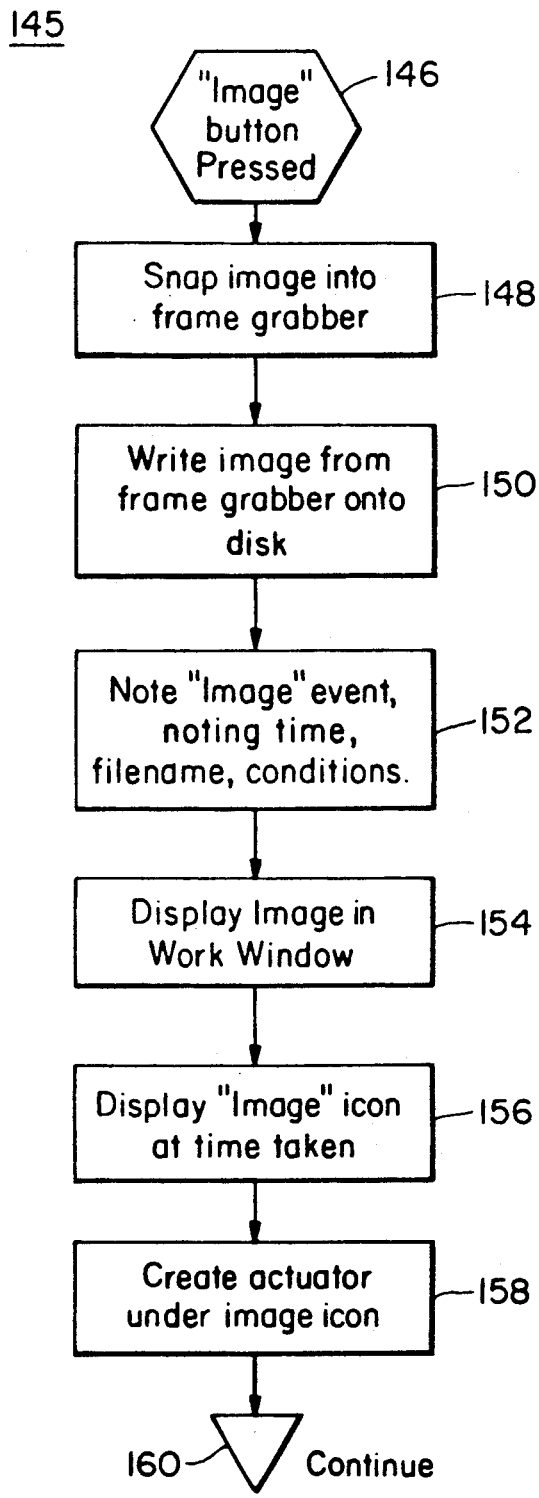
FIG. 7 is a flow chart showing the acquisition of an image by the system.

Flow chart 145, FIG. 7, enters data by viewer activation of a button. In this example an image taking button 44 as depicted in FIG. 3 is activated 146. The activation of this button instructs the system to activate the frame grabber 148 which digitizes an instantaneous image input by an imaging device such as a video camera. This image data is then written onto a disk for storage 150. The image data is marked as an event with appropriate categorizations 152, in this example, time of input, file name and the prevailing conditions. The image is then displayed by the system in the work window 42 as depicted in FIG. 3. A pictorial icon of the image is then created and displayed 156 relative to the indexing dimension, in this example time of creation. Such an icon 50 is depicted in FIG. 3. An actuator 54 is then created 158, as depicted in FIG. 3, around the pictorial icon to allow future access of the data of the image. The system then continues 160 awaiting the next input instruction.

Figure 8:
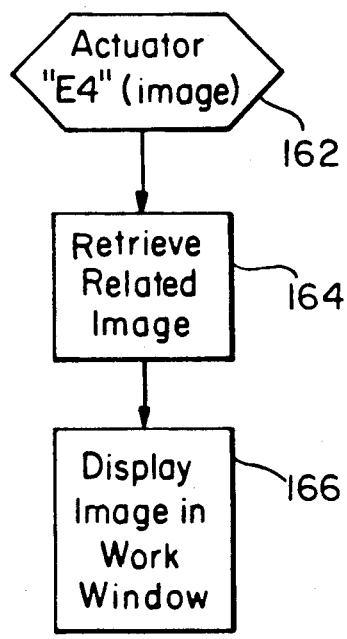
FIG. 8 is a flow chart showing the retrieval of an image through activation of a pictorial icon.

Flow chart 161, FIG. 8, describes the retrieval of data through the operation of an actuator placed around a pictorial icon. An actuator placed around a pictorial icon is activated 162 by interacting with the screen either by a physical touch of the active area or through use of a cursor. Activation of the icon serves to retrieve the data object into system memory 164, in this example a stored image. The system then displays this image in the work window 166.

Figure 9:
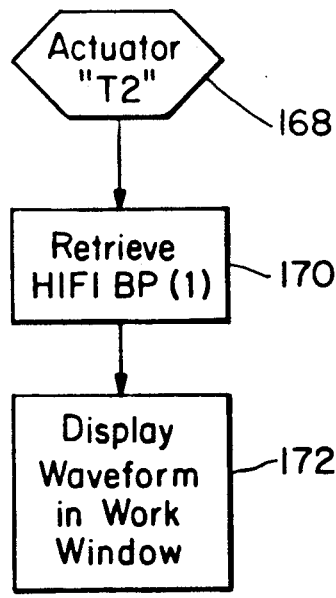
FIG. 9 is a flow chart showing the retrieval of a high fidelity blood pressure waveform data object through activation of an actuator.

Flow chart 169, FIG. 9, similar to the method for retrieving data from an icon, shows the retrieval of trend event related data through the activation of a trend event located actuator 66 as depicted in FIG. 3.

An actuator located around a group of trends on the indexing dimension comprising a trend event is operated 168 by user interaction with the display screen, either through physical touch or cursor contact. This actuator activation causes the system to retrieve a related data object 170, in this example high-fidelity waveform data. This waveform is then displayed in the work window 172.

Figure 10:
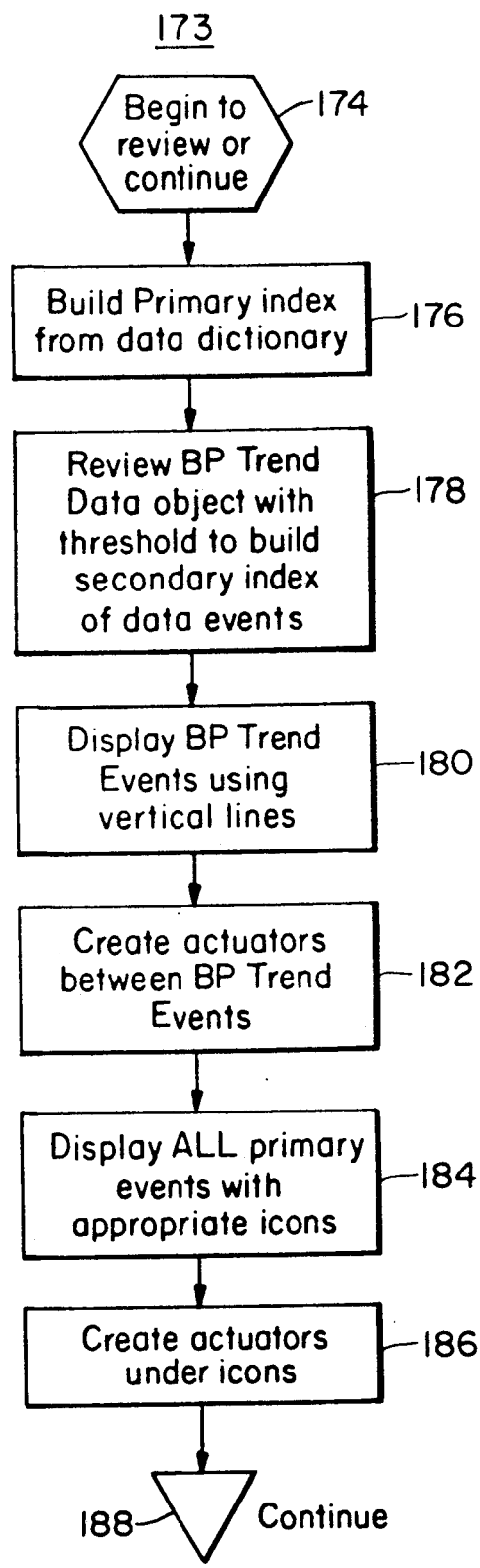
FIG. 10 is a flow chart showing the continuing operation of the system.

Finally, flow chart 173, FIG. 10, describes the continuing operation of the system. The system will either review previous collected data or continue building in new data 174. An initial dictionary of new data is indexed into a primary index of trend data events 176. These trend data events then form the basis for the creation of trend data objects. The data objects are, in turn, reviewed to build a secondary index of data events based upon the information present in the data objects 178, in this example, blood pressure waveform data objects. Trend events are then displayed by the system using vertical line plots 180. Actuators are then created for each trend event to retrieve associated data objects 182. All primary events, including those generated from data objects, are then displayed using predetermined pictorial icons which describe the type of underlying events 184. Actuators are then created to activate these pictorial icons in order to retrieve the underlying data objects represented by the icons. Finally, the system returns to repeat this process.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. An interactive record system for automatically organizing and indexing data obtained from a number of internal and external input sources, comprising:
   means for organizing a set of data along at least one indexing dimension;
   means for identifying specific data events from said set of data according to predetermined methods;
   means for establishing an index of data objects associated with said specific data events;
   means for displaying said index of data objects and specific data events along said indexing dimension; and
   means for defining actuators for manipulating said data objects indexed with said specific data events.

2. The interactive record system of claim 1 in which said means for establishing an index of data objects includes marker means for individually marking said specific data events.

3. The interactive record system of claim 2 in which said marker means includes means for designating the location of data associated with said specific data events.

4. The interactive record system of claim 2 in which said marker means includes means for specifying the configuration of said actuators.

5. The interactive record system of claim 2 in which said marker means includes means for determining a symbolic representation to be displayed for said data objects.

6. The interactive record system of claim 2 in which said marker means includes means for designating the operation to be effected for a specific data event.

7. The interactive record system of claim 1 in which said means for defining actuators include means for bounding interactive areas on a display screen corresponding to locations along said indexing dimension.

8. The interactive record system of claim 7 in which said means for bounding includes means for operating said actuators in response to a touching of said interactive areas.

9. The interactive record system of claim 7 in which said means for bounding includes means for operating said actuators in response to a contacting of said interactive areas with a cursor.

10. The interactive record system of claim 1 in which said means for displaying includes means for generating descriptive pictorial icons which are symbolic representations of said data objects and said specific data events and which are associated with said specific data events along said indexing dimension.

11. The interactive record system of claim 1 in which said means for organizing includes an indexing dimension which is time.

12. The interactive record system of claim 1 in which said means for identifying specific data events includes means for comparing said set of data to a reference.

13. The interactive record system of claim 1 in which said means for identifying specific data events includes means for reviewing data objects to generate additional specific data events.

14. The interactive record system of claim 1 in which said means for organizing a set of data includes means for graphically plotting said set of data on a display screen.

15. The interactive record system of claim 14 in which said means for graphically plotting includes means for graphically displaying minimum, maximum and mean values of data over a given interval.

16. The interactive record system of claim 1 in which said means for establishing includes a data object comprising at least one of a plurality of data fields including audio, visual, textual, numerical, algorithmic and graphical data.

17. An interactive record system for automatically organizing and indexing data obtained from a number of internal and external input sources, comprising:
   means for organizing a set of data relative to at least one indexing dimension;
   means for identifying specific data events from said set of data according to predetermined methods;
   means for plotting said specific data events on a display screen along an axis representative of said indexing dimension;
   means for establishing an index of data objects from internal sources and external sources associated with said specific data events;
   means for displaying said index of data objects and said specific data events relative to said specific data events; and
   means for defining actuators associated with said specific data events for manipulating said data objects.

18. The interactive record system of claim 17 in which said means for establishing an index of data objects includes means for individually marking said specific data events.

19. The interactive record system of claim 18 in which said marker means includes means for designating the location of data associated with said specific data events.

20. The interactive record system of claim 18 in which said marker means includes means for specifying the configuration of said actuators.

21. The interactive record system of claim 18 in which said marker means includes means for determining a symbolic representation to be displayed for a data object.

22. The interactive record system of claim 18 in which said marker means includes means for designating the operation to be effected for a specific data event.

23. The interactive record system of claim 17 in which said means for identifying specific data events includes means for reviewing data objects to generate additional specific data events.

24. The interactive record system of claim 17 in which said means for defining actuators includes means for bounding interactive areas on a display screen corresponding to locations along said axis.

25. The interactive record system of claim 24 in which said means for bounding includes means for operating said actuators in response to a touching of said interactive areas.

26. The interactive record system of claim 24 in which said means for bounding includes means for operating said actuators in response to a touching of said interactive areas.

27. The interactive record system of claim 17 in which said means for displaying includes means for generating descriptive pictorial icons which are symbolic representations of said data objects and said specific data events and which are associated with said specific data events along said indexing dimension.

28. The interactive record system of claim 17 in which said means for establishing includes a data object comprising at least one of a plurality of data fields including audio, visual, textual, numerical, algorithmic and graphical data.

29. The interactive record system of claim 17 in which said means for displaying includes display control means for representing data on said axis in magnified and reduced format.

30. A medical interactive record system for automatically organizing and indexing data obtained from a number of patient monitoring source comprising:
means for organizing a set of monitored data relative to time;
means for determining desired values of data taken over a given interval of time;
means for representing said values on a display screen as linear trends relative to a point displayed on an axis representing time;
means for identifying specific data events from said trends that are greater than or less than predetermined threshold values;
means for establishing an index of data objects from automatic inputs, from internally generated data and from data input manually associated with said specific data events;
means for displaying said index of data objects associated with said specific data events using pictorial icons that symbolically represent said data objects;
means for defining actuators associated with said specific data events for manipulating said data objects;
means for operating said actuators in response to a touching by at least one of a cursor touch and a physical touch; and
means for accessing said data objects in response to a touching by at least one of a cursor touch and a physical touch.

31. The medical interactive record system of claim 30 in which said means for establishing includes a data object comprising at least one of a plurality of data fields including audio, visual, textual, numerical, algorithmic and graphical data.

32. The medical interactive record system of claim 30 in which said means for establishing includes means for signifying the type of data objects to be created for said specific data events.

33. The medical interactive record system of claim 30 in which said means for displaying includes display control means for representing data on said axis in magnified and reduced format.

34. A medical interactive record system for use in a cardiac catheterization laboratory for automatically organizing and indexing data obtained from a physiological monitor, comprising:
means for organizing a set of physiological data relative to time of input;
means for determining the high, low and means values taken over a given interval of time;
means for graphing said values on a display screen as vertical line trends relative to a point displayed on a horizontal axis representing time of input;
means for identifying specific physiological events from said trends that cross a predetermined threshold value;
means for establishing an index of data objects from physiological monitor data, internally generated data, automatically input data and data input by personnel, associated with said specific physiological events;
means for displaying said index of data objects relative to said specific physiological events using pictorial icons that symbolically represent said data objects;
means for creating actuators associated with said trends in order to manipulated said data objects;
means for operating said actuators in response to a touching by at least one of a cursor touch and a physical touch; and
means for accessing said data objects in response to a touching by at least one of a cursor touch and a physical touch.

* * * * *